United States Patent
Huang et al.

(10) Patent No.: US 9,895,303 B2
(45) Date of Patent: Feb. 20, 2018

(54) PEPTIDE, METHOD AND COMPOSITION FOR STIMULATING MELANOGENESIS

(71) Applicant: Renorigin Innovation Institute Co., Ltd., Taipei (TW)

(72) Inventors: Hsiu-Chin Huang, Taipei (TW); Hsuan Lin, Taipei (TW)

(73) Assignee: RENORIGIN INNOVATION INSTITUTE CO. LTD., Taipei (TW)

( * ) Notice: Subject to any disclaimer, the term of this patent is extended or adjusted under 35 U.S.C. 154(b) by 0 days.

(21) Appl. No.: 15/051,290

(22) Filed: Feb. 23, 2016

(65) Prior Publication Data
US 2017/0239161 A1 Aug. 24, 2017

(51) Int. Cl.
*A61K 38/00* (2006.01)
*A61K 8/64* (2006.01)
*A61Q 5/00* (2006.01)
*A61Q 5/02* (2006.01)
*A61Q 5/12* (2006.01)

(52) U.S. Cl.
CPC ............... *A61K 8/64* (2013.01); *A61Q 5/004* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| 2010/0135944 A1* | 6/2010 | Chen | A61K 8/35 424/63 |
| 2012/0034182 A1* | 2/2012 | Hoffmann | A61Q 5/12 424/70.9 |

FOREIGN PATENT DOCUMENTS

WO  WO 2007/068401  *  6/2007

OTHER PUBLICATIONS

Redkal et al. (J. Peptide Sci. 5: 32-45, 1999).*
Ishii et al., Biochem Cell Biol. Feb. 2017;95(1):119-125. doi: 10.1139/bcb-2016-0053. Epub Jan. 19, 2017 (Year: 2017).*

* cited by examiner

*Primary Examiner* — Jennifer Pitrak McDonald
*Assistant Examiner* — Sergio Coffa
(74) *Attorney, Agent, or Firm* — Birch, Stewart, Kolasch & Birch, LLP

(57) ABSTRACT

An isolated peptide for stimulating melanogenesis in a mammal subject is provided. The isolated peptide consisting of an amino acid sequence of FKCRRWQWRMK KLGAPSI (SEQ ID NO: 1). Also provided are methods and compositions for stimulating melanogenesis in a mammal subject.

8 Claims, 3 Drawing Sheets
(3 of 3 Drawing Sheet(s) Filed in Color)

Control

Kojic acid 400 µM

IBMX 100 µM

LIB 17-34 (50 µg/ml)

PEPTIDE, METHOD AND COMPOSITION FOR STIMULATING MELANOGENESIS

REFERENCE TO SEQUENCE LISTING SUBMITTED VIA EFS-WEB

This application includes an electronically submitted sequence listing in .txt format. The .txt file contains a sequence listing entitled "2016-05-11 5992-0135PUS1 ST25.txt" created on May 11, 2016 and is 542 bytes in size. The sequence listing contained in this .txt file is part of the specification and is hereby incorporated by reference herein in its entirety.

FIELD OF THE INVENTION

The present invention relates generally to a peptide for increasing melanogenesis or increasing the melanin content in mammals, and methods and compositions thereof.

BACKGROUND OF THE INVENTION

Hair color is determined by the relative amounts of the brown-black pigment eumelanin and the red-yellow pigment pheomelanin in follicular melanocytes. Increasing melanogenesis leads to increasing the melanin content of melanocytes, and hence results in increased pigmentation or darkened color of the skin, hair wool or fur.

U.S. Pat. No. 5,352,440 is directed to increasing melanin synthesis in melanocytes and increasing pigmentation by administration of certain diacylglycerol compounds. U.S. Pat. No. 5,532,001 is directed to increasing pigmentation in mammalian skin via administration of certain DNA fragments. U.S. Pat. No. 5,554,359 is directed to increasing levels of melanin in melanocytes by administration of lysosomotropic agents.

BRIEF SUMMARY OF THE INVENTION

It is unexpectedly found in the present invention that a peptide with the sequence FKCRRWQWRMKKLGAPSI (SEQ ID NO: 1) is active in stimulating or increasing melanogenesis in a mammal subject.

Accordingly, the present invention provides in one aspect an isolated peptide for stimulating melanogenesis in a mammal subject or increasing the melanin content of mammalian melanocytes. The isolated peptide consists of an amino acid sequence of SEQ ID NO: 1.

In another aspect, the present invention features a method for darkening the hair color in a human subject, which comprises administering to said subject or said melanocytes an effective amount of an isolated peptide according to the present invention in the amount effective to stimulate melanogenesis in a mammal subject or melanocytes.

In an embodiment of the invention, the melanin content of mammalian is increased through the stimulation of melanogenesis by the isolated peptide. In preferred embodiments of the invention, the method is used to darkening the hair color of the mammal subject, such as a human subject. In preferred embodiments of the invention, the isolated peptide is administered topically to the subject.

In one further aspect, the present invention provides a composition for stimulating melanogenesis in a mammal subject or increasing the melanin content of mammalian melanocytes. The composition comprises an effective amount of an isolated peptide consisting of the amino acid sequence of SEQ ID NO: 1. According to certain embodiments of the invention, the composition may further comprise an acceptable carrier, and may be formulated as a topical formulation.

According to the present invention, the topical formulation may comprise an ointment, lotion, cream, gel, drops, spray, liquid, shampoo or hair conditioner. In one preferred embodiment, the composition is formulated as a shampoo or a hair conditioner.

It is to be understood that both the foregoing general description and the following detailed description are exemplary and explanatory only and are not restrictive of the invention.

BRIEF DESCRIPTION OF THE SEVERAL VIEWS OF THE DRAWINGS

The patent or application file contains at least one drawing executed in color. Copies of this patent or patent application publication with color drawings will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1A:
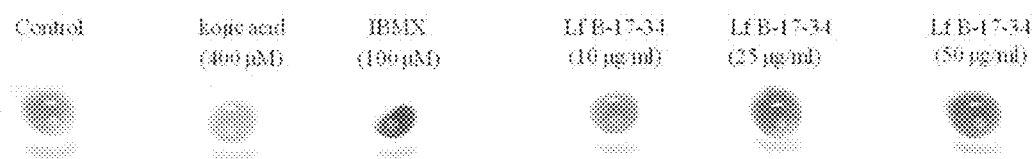
Figure 1B:
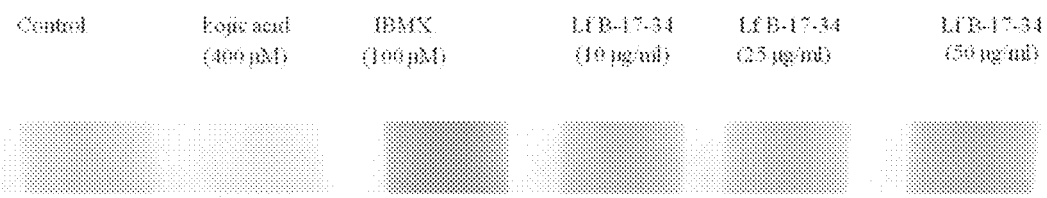

FIG. 1A shows the hyper pigmentation by the peptide of the invention in cells. FIG. 1B shows the hyper pigmentation by the peptide of the invention in culture medium. B16F10 melanoma cells were treated with 10-50 μg/ml peptide of SEQ ID NO: 1 ("Lf B-17-34") for 5 days with a medium change at day 3. The cells and medium were recovered in test tubes. Kojic acid is used as negative control in the cellular study due to known inhibitory effects on tyrosinase activity. IBMX is used as positive control in the cellular study due to known elevator of cellular cAMP level, to stimulate melanogenesis.

Figure 2A:
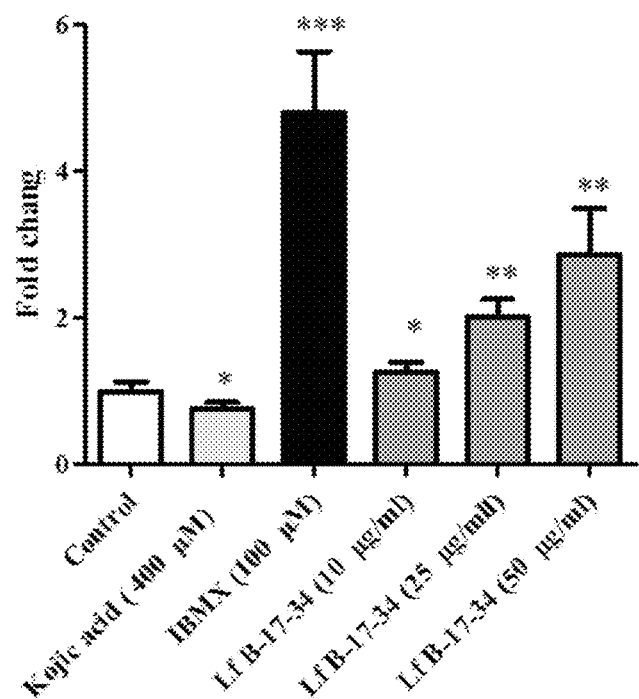
Figure 2B:
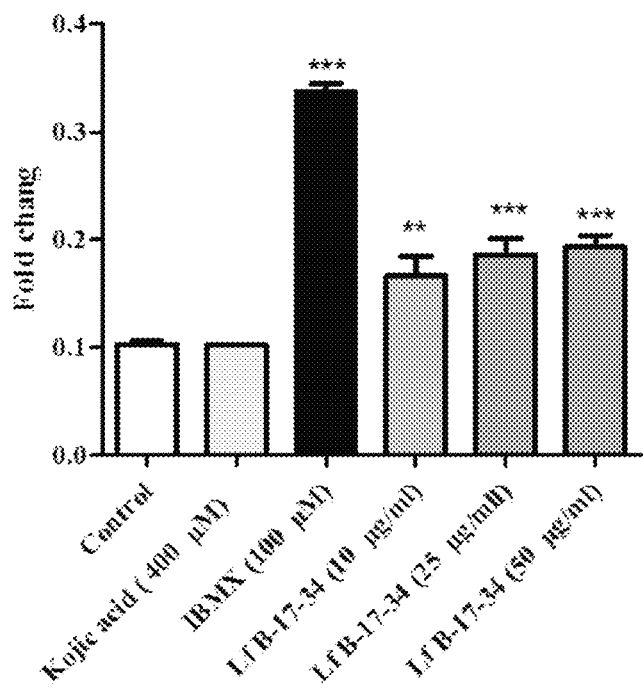

FIG. 2A shows the melanin content in cells. FIG. 2B shows the melanin secretion in culture medium. Each measurement was made in triplicate and data shown represent the mean±S.D. *$p<0.05$ compared to control.

Figure 3:
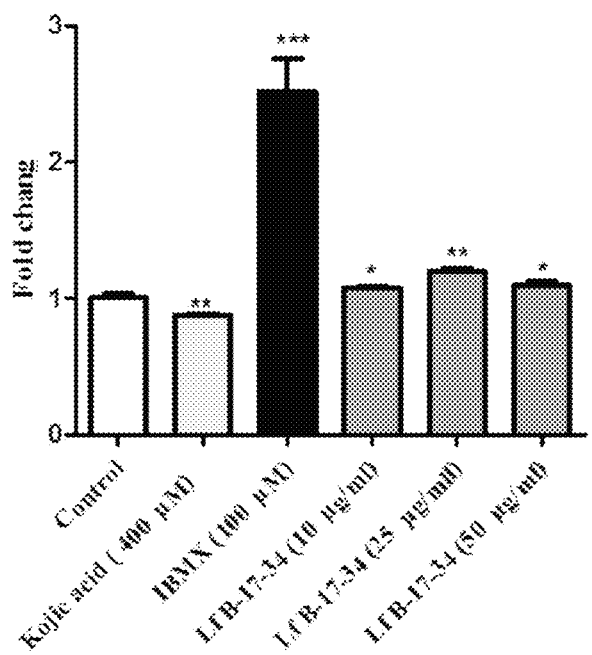

FIG. 3 shows the tyrosinase activity increased by the peptide of the invention. *$p<0.05$ compared to control.

Figure 4:
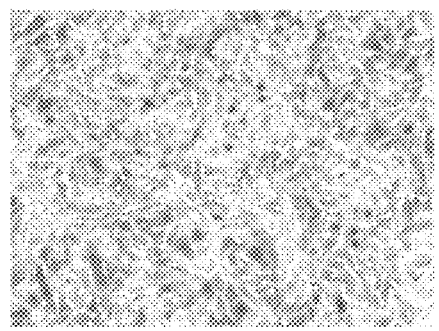
Figure 4:
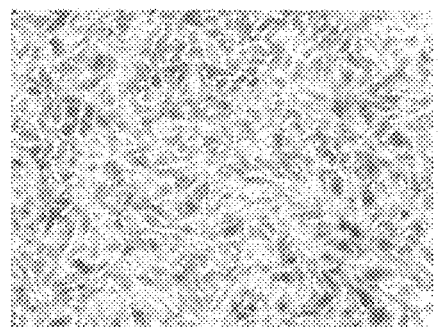
Figure 4:
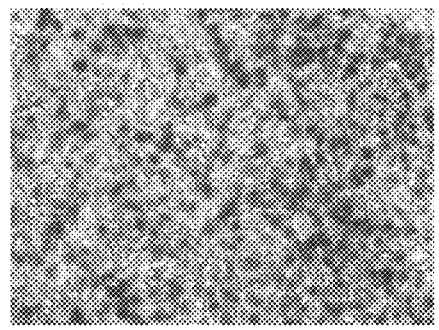
Figure 4:
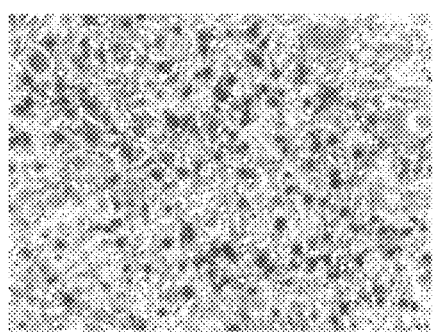

FIG. 4 shows the results of DOPA staining.

DETAILED DESCRIPTION OF THE INVENTION

In one aspect, the present invention features an isolated peptide for stimulating melanogenesis in a mammal subject or increasing the melanin content of mammalian melanocytes, the isolated peptide consisting of an amino acid sequence of FKCRRWQWRM KKLGAPSI (SEQ ID NO: 1).

In another aspect, the invention provides a method for stimulating melanogenesis in a mammal subject or increasing the melanin content of mammalian melanocytes. The method comprises a step of administering to said mammal subject or said mammalian melanocytes the isolated peptide of SEQ ID NO: 1, in an amount effective to stimulate melanogenesis in the mammal subject, or in an amount effective to increase the melanin content of said melanocytes. Preferably, the isolated peptide is administered topically.

In some preferred embodiments of the invention, the method is used to darkening the hair color of the mammal subject, such as a human subject.

In yet another aspect, the present invention provides a composition comprising an effective amount of an isolated peptide consisting of the amino acid sequence of SEQ ID NO: 1. The composition of the present invention is useful in stimulating melanogenesis or increasing the melanin content of melanocytes in mammals. The composition may be used for cosmetic purposes, for example, darkening hair color.

In certain embodiments of the invention, the composition further comprises a (physiologically) acceptable carrier.

In some preferred embodiments, the composition of the present invention is formulated as a topical formulation.

Unless defined otherwise, all technical and scientific terms used herein have the same meaning as commonly understood by those of ordinary skill in the art to which this invention belongs.

The use of the word "a" or "an" when used in conjunction with the term "comprising" in the claims and/or the specification may mean "one," but it is also consistent with the meaning of "one or more," "at least one," and "one or more than one."

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

As used herein, the term "carrier" refers to materials commonly used on the formulation of pharmaceutical or cosmetic composition used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" is used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

The present invention contemplates the use of the isolated peptide of SEQ ID NO: 1 as an active ingredient for various uses. In one preferred embodiment, the isolated peptide of the present invention is combined with an acceptable carrier to form a topical formulation which may be placed on the skin. Topical formulations may comprise an ointment, lotion, paste, cream, gel, drop, suppository, spray, liquid, shampoo, hair conditioner, powder and transdermal patch. Thickeners, diluents, emulsifiers, dispersing aids or binders may be used as needed. Preferably, one function of the carrier is to enhance skin penetration of the peptide of the present invention, and should be capable of delivering the peptide to melanocytes under in vivo conditions. Suitable carriers are well known to one of ordinary skill, and include but are not limited to water, dimethylsulfoxide, ethanol, liposome, liquid petrolatum, petrolatum dimethylformamide, 2-pyrrolidone, oleic acid, and Azone® brand penetration enhancer.

The present invention is further illustrated by the following examples, which are provided for the purpose of demonstration rather than limitation.

EXAMPLES

Example 1: Peptide of SEQ ID NO: 1 Stimulates Melanogenesis in Mouse Melanoma Cells 1. Materials and Methods 1.1 Preparation of Isolated Peptide of SEQ ID NO: 1

The peptide with the amino acid sequence of FKCRRWQWRMK KLGAPSI (SEQ ID NO: 1) (2291.83 Da), derived from bovine lactoferricin (LfcinB), were synthesized by MDBio, Inc. (Taipei, Taiwan). The purity and composition of the peptide were confirmed by high performance liquid chromatography (HPLC) and mass spectrometry. A 10 mg/ml sample of peptide of SEQ ID NO: 1 was produced by dissolving 10 mg of peptide powder and mixed with 1 ml double deionized water ($ddH_2O$), stored at $-20°$ C. before use.

1.2 Cell cultures

B16F10 murine melanoma cells were cultured in phenol red-free DMEM with 10% fetal bovine serum and penicillin/streptomycin (100 IU/50 g per mL) in a humidified atmosphere containing 5% $CO_2$ in air at 37° C.

1.3 Melanin Content Assay

Melanin contents of cultured B16F10 cells were measured according to the method (Lee et al., J Invest Dermatol 124, 405-411, 2005) with a slight modification. Briefly, B16F10 cells were seeded in 6-well plate ($2×10^4$ cells/well) and incubated overnight to allow cells to adhere. After treating with various test samples in an incubator for 5 days, washed, trypsinized and counted before pelleting. Melanin per cell was quantified after boiling in 1 M NaOH for 1 hour and melanin content in each sample was read from a calibration curve against synthetic eumelanin at 400 nm and converted to means±SE melanin pg/cell from 3 independent experiments.

1.4 Tyrosinase Assay

Tyrosinase is the rate limiting enzyme in the melanogenic pathway. Its measurement provides a highly specific and sensitive indication of degree of induction of melanogenesis. Tyrosinase enzyme activity of cultured B16F10 cells were measured according to the method of (Bellei et al., J Biol Chem 285, 7288-7299, 2010) with a slight modification. Briefly, B16F10 cells were seeded in 6-well plate ($2×10^4$ cells/well) and incubated overnight to allow cells to adhere. After treating with various test samples in an incubator for 5 days, cells were washed with PBS and then harvested using trypsin. At the end point, the cells were solubilized with phosphate buffer (pH 6.8) containing 1% Triton X-100. The cells were then disrupted by freezing and thawing, and the lysates were clarified by centrifugation at 10,000×g for 10 min. After protein quantification and adjustment of protein concentrations with lysis buffer, 100 μl of each lysate (each containing the same amount of protein) were aliquoted into the wells of a 96-well plate, and 100 μl of 5 mM L-DOPA were then added to each well. The absorbance was measured spectrophotometrically at 475 nm following a 30-mM incubation period at 37° C. The measurement was repeated three times.

1.5 DOPA Staining

DOPA staining was also performed to measure tyrosinase enzyme activity. B16F10 cells were seeded in 6-well plate ($2\times10^4$ cells/well) and incubated overnight to allow cells to adhere. After treating with various test samples in an incubator for 4 days, cells were washed with PBS, fixation with 2% paraformaldehyde and washing with PBS a further three times, the cells were incubated with 0.1% DOPA (dissolved in 0.1 M PBS) at 37° C. for 5 hour, and observed using light microscopy (Wang et al., Exp Ther Med 6, 967-972, 2013).

2. Results 2.1 Effects on Melanogenesis

Cultures of B16F10 cells treated with 10-50 μg/ml peptide of SEQ ID NO: 1 ("Lf B-17-34") showed hyper pigmentation in cells as in medium to a similar extent (FIGS. 1A and 1B).

2.2 Effects on Melanin Contents

B16F10 cells treated with 10-50 μg/ml peptide of SEQ ID NO: 1 ("Lf B-17-34") showed significantly increased melanin synthesis in a concentration-dependent manner (FIGS. 2A and 2B).

2.3 Effects on Tyrosinase Activity

B16F10 cells treated with 10-50 μg/ml peptide of SEQ ID NO: 1 ("Lf B-17-34") showed significantly increased tyrosinase activity (FIG. 3) and the cells also showed strong DOPA staining (FIG. 4).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

---

---

What is claimed is:

1. A composition for stimulating melanogenesis in a mammal subject, comprising an effective amount of a peptide consisting of the amino acid sequence of SEQ ID NO: 1, which is formulated as a topical formulation in the form of an ointment, lotion, cream, gel, shampoo or hair conditioner.

2. The composition of claim 1, further comprising a physiologically acceptable carrier.

3. The composition of claim 1, wherein the topical formulation is a shampoo.

4. The composition of claim 1, wherein the topical formulation is a hair conditioner.

5. The composition of claim 1, which is effective for darkening the hair color in a human subject.

6. A method for darkening the hair color in a human subject, which comprises administering to said subject an effective amount of the composition of claim 1 in the amount effective to stimulate melanogenesis in the human subject or melanocytes.

7. The method of claim 6, wherein the melanin content is increased through the stimulation of melanogenesis by the composition.

8. The method of claim 6, wherein the composition is administered to the subject topically.

* * * * *

SEQUENCE LISTING

```
<160> NUMBER OF SEQ ID NOS: 1

<210> SEQ ID NO 1
<211> LENGTH: 18
<212> TYPE: PRT
<213> ORGANISM: Bos taurus

<400> SEQUENCE: 1

Phe Lys Cys Arg Arg Trp Gln Trp Arg Met Lys Lys Leu Gly Ala Pro
1               5                   10                  15

Ser Ile
```